United States Patent
Till et al.

(10) Patent No.: US 6,923,955 B2
(45) Date of Patent: Aug. 2, 2005

(54) PRESBYOPIA TREATMENT BY LENS ALTERATION

(75) Inventors: Jonathan S. Till, Salem, VA (US); Ronald D. Blum, Roanoke, VA (US)

(73) Assignee: Newlens, LLC, Roanoke, VA (US)

( * ) Notice: Subject to any disclaimer, the term of this patent is extended or adjusted under 35 U.S.C. 154(b) by 454 days.

(21) Appl. No.: 10/050,879

(22) Filed: Jan. 18, 2002

(65) Prior Publication Data

US 2002/0110549 A1 Aug. 15, 2002
US 2004/0213774 A9 Aug. 15, 2002

Related U.S. Application Data

(63) Continuation-in-part of application No. 09/930,287, filed on Aug. 16, 2001.
(60) Provisional application No. 60/262,423, filed on Jan. 19, 2001, and provisional application No. 60/225,659, filed on Aug. 16, 2000.

(51) Int. Cl.$^7$ ............................................. A61K 31/74
(52) U.S. Cl. .................................................. 424/78.04
(58) Field of Search ............................. 424/78.04, 489, 424/499

(56) References Cited

U.S. PATENT DOCUMENTS

| | | | |
|---|---|---|---|
| 817,630 A | * | 4/1906 | Delaunay-Belleville ...... 514/18 |
| 5,395,356 A | | 3/1995 | King et al. ............... 606/4 |
| 5,459,133 A | | 10/1995 | Neufeld ................. 514/215 |
| 5,465,737 A | | 11/1995 | Schachar |
| 5,488,050 A | | 1/1996 | Neufeld |
| 5,503,165 A | | 4/1996 | Schachar |
| 5,527,774 A | | 6/1996 | Girard |
| 5,529,076 A | | 6/1996 | Schachar |
| 5,665,770 A | | 9/1997 | Terao et al. |
| 5,722,952 A | | 3/1998 | Schachar |
| 5,772,952 A | | 6/1998 | Allen et al. |
| 5,843,184 A | | 12/1998 | Cionni |
| 5,874,455 A | | 2/1999 | Terao et al. ............. 514/381 |
| 5,888,243 A | | 3/1999 | Silverstrini |
| 6,013,462 A | | 1/2000 | Kauvar et al. |
| 6,214,044 B1 | | 4/2001 | Silverstrini |

FOREIGN PATENT DOCUMENTS

| | | |
|---|---|---|
| EP | 0 369 880 | 5/1990 |
| WO | WO 93/25166 | 12/1993 |
| WO | WO 02/13863 | 2/2002 |

OTHER PUBLICATIONS

Krumdieck et al.: *Mechanism of Homocysteine Toxicity on Connective Tissues: Implications for the Morbidity of Aging,* J. Nutr. 2000, 130 (2S suppl):365S–368S.

Ronald R. Krueger, MD, MSE, et al., "Experimental increase in accomodative potential after neodymium: yttrium–aluminum–garnet laser photodisruption of paired cadaver lenses", Ophthalmology (2001), pp. 108: 2122–2129.

Paper entitled "Experimental increase in accommodative potential after neodymium:yttrium–aluminum–garnet laser photodisruption of paired cadaver lenses," by Ronald R. Krueger, MD, MSE, et al.; from Ophthalmology (2001) pp. 108: 2122–2129.

* cited by examiner

*Primary Examiner*—Carlos A. Azpuru
(74) *Attorney, Agent, or Firm*—Kenyon & Kenyon

(57) ABSTRACT

This invention effects a change in the accommodation of the human lens affected by presbyopia through the use of various reducing agents that change accommodative abilities of the human lens, and/or by applying energy to affect a change in the accommodative abilities of the human lens. This invention both prevents the onset of presbyopia as well as treats it. By breaking and/or preventing the formation of bonds that adhere lens fibers together causing hardening of the lens, the present invention increases the elasticity and distensibility of the lens and/or lens capsule.

22 Claims, No Drawings

PRESBYOPIA TREATMENT BY LENS ALTERATION

The instant application is a continuation-in-part of the co-pending utility application Ser. No. 09/930,287 filed Aug. 16, 2001 and entitled "Presbyopia Treatment by Lens Alteration," from which priority is claimed under 35 U.S.C. §120. application Ser. No. 09/930,287 in turn claims priority under 35 U.S.C. §120 to provisional application Ser. No. 60/225,659 filed Aug. 16, 2000, from which priority is again claimed herein under 35 U.S.C. §120. The instant application further claims priority under 35 U.S.C. §120 to provisional application Ser. No. 60/262,423 filed Jan. 19, 2001.

FIELD OF THE INVENTION

The present invention relates to a method and device for reversing and treating presbyopia.

BACKGROUND OF THE INVENTION

Presbyopia affects virtually every person over the age of 44. According to Jobson Optical Database, 93% of people 45 and over are presbyopic. Presbyopia entails the progressive loss of amplitude of accommodation that occurs with aging. Adler's Physiology of the Eye, which is incorporated herein by reference, discloses that the human accommodative amplitude declines with age such that accommodation is substantially eliminated by the age of 50 to 55. Accommodative ability, as defined by U.S. Pat. No. 5,459,133 to Neufeld and incorporated in its entirety herein by reference for background information, is the capacity of the eye to focus for near vision by changing the shape of the lens to become more convex.

The ocular tissues involved in the accommodative response include the lens, the zonules, the lens capsule, and the ciliary muscle. Of these, the lens is the central tissue. These structures function together to enable the eye to focus on close objects by changing the shape of the lens. The lens is centrally suspended between the anterior and posterior chambers behind the pupillary opening of the iris. The lens is supported by an array of radially oriented zonular fibers, which extend from the lateral edges of the lens to the inner border of the circumferential ciliary muscle. The ciliary muscle is attached to the scleral coat of the eye. When the eye is at rest, it is focused for distance and the lens is in a somewhat flattened or less convex position. This shape is due to the tension that is exerted on the lens periphery by the zonules. The zonules pull the edges of the lens toward the ciliary body.

During accommodation, the shape of the lens becomes more convex through contraction of the ciliary muscle, which allows the ciliary attachment of the zonules to move toward the lens, reducing the tension in the anterior zonules. This reduction in tension allows the central region of the lens to increase in convexity, thereby enabling near objects to be imaged on the retina. The processes involving the coordinated effort of the lens, zonules, ciliary body, medial rectus muscles and iris, among others, that leads to the ability of the eyes to clearly focus near on the retina is the accommodative process.

Several theories have been advanced to explain the loss of accommodation with age. These theories include the hardening of the lens with age, loss of strength in the ciliary muscle, factors related to the physical growth of the lens, and, the loss of elasticity of the lens capsule. As for the loss of strength of the ciliary muscle, it is noted that although there are age-related morphological changes that occur, there is little evidence of diminishing strength of the ciliary muscle. In fact, under the influence of pilocarpine, the ciliary muscle will vigorously contract even in presbyopic eyes.

The lens grows throughout one's life and theories have been proposed that it is this increase in size that prohibits the effects of the zonules from affecting a change in the shape of the lens. Recent works exploring this possibility have not met widespread acceptance thus far. Most of the growth of the lens is not in its diameter, but instead, in its anterior-posterior dimensions.

As for changes in the lens capsule, it has been postulated that reduction in the elasticity of the capsule is, in fact, a contributing factor in presbyopia. Moreover, it has been found that Young's modulus of elasticity for the lens capsule decreases by nearly 50% from youth to age 60, while accommodation decreases by 98%. Consequently, the principal cause of presbyopia is now considered to be "lenticular sclerosis" or the hardening of the lens.

A cataract is a condition in which the lens becomes less clear. The study of cataracts lends insight into lens and capsular changes. The usual senile cataract is relatively discus-shaped when removed from the eye, its shape being dictated by the firm lens substance. The liquefied hypermature cataract is globular when extracted, rounded up by the elastic lens capsule. This is indirect evidence that it may be possible to reverse the lenticular changes associated with presbyopia, and that the lens capsule is still sufficiently elastic.

At the present time, common treatments for presbyopia include reading glasses, bifocal glasses, or mono-vision contact lenses. All of these solutions necessitate the use of an appliance creating additional shortcomings.

Alternative theories for treating presbyopia include scleral expansion and corneal reshaping. The efficacy of such techniques is not well-established and, importantly, these techniques do not attempt to reverse what the inventors of the subject-application believe to be a substantial causation, as explained more fully below, in the loss of the accommodative amplitude of the lens typically associated with the normal aging process. Moreover, because scleral expansion and corneal reshaping involve macroscopic changes in the morphology of the lens and/or cornea it fails to reverse presbyopia.

Finally, the use of the excimer laser for the purposes of corneal reshaping to produce a multifocal refracting surface has been disclosed in U.S. Pat. No. 5,395,356. While this method seems promising, it still requires structural changes to the cornea to compensate for aging changes in the lens. Rather than trying to undo the changes brought on by presbyopia, techniques such as these merely compensate for the loss of accommodative function by altering another ocular structure.

SUMMARY OF THE INVENTION

While not wishing to be bound to any particular theory, it is now believed that presbyopia is caused by the hardening of the lens, which can be due to an alteration of the structural proteins or an increased adhesion between the lens fibers. It is also believed that the intralenticular viscosity increases with age as a result of the formation of certain chemical bond structures within the lens. Accordingly, the present invention is directed to method and apparatus for preventing and or reversing presbyopia through treatment of the lens such that the viscosity of the lens is reduced, restoring the elasticity and movement to the lens fibers and increasing the accommodative amplitude of the lens.

The claimed invention is also directed to a method of reversing or treating presbyopia resulting in underlying changes in the structures and/or interactions of molecules comprising those components of the eye associated with the accommodative process, most notably the lens and/or lens capsule.

In an embodiment, the present invention provides a novel molecular approach to reversing presbyopia by restoring the accommodative amplitude of the lens, and in another preferred embodiment, to reversing presbyopia while also reducing the tendency for the lens to lose its thus restored accommodative amplitude.

In another embodiment of the invention the onset of presbyopia is prevented by regularly administered treatment where elasticity and the accommodative ability of the lens is restored. By applying the treatments as described herein to the eyes of persons in their mid to late 30's, or even younger, the on-set of presbyopia, as defined by a loss of accommodation, such that the accommodative power of the eye is below 2.5 Diopters, can be avoided. In one embodiment of the invention, such treatments whether for the purposes of preventing or reversing presbyopia, would be occasionally repeated during the course of a patient's lifetime. The frequency of the treatment would be determined by the degree of accommodative loss that needs to be recovered, the amount of accommodation that can be safely restored in a single procedure, and the amount of restoration desired.

In one embodiment, the present invention is directed to a method for reversing and/or treating presbyopia by breaking disulfide bonds in molecules comprising the structures of the eye, most notably the lens and the lens capsule, in which disulfide bonds are believed to be a substantial factor in the progressive loss of accommodative amplitude. In another embodiment, the breaking of the disulfide bonds is accompanied by chemical modification of the sulfur moiety in the cysteine molecule formed upon breaking of the disulfide bonds, such chemical modification rendering the sulfur moiety less likely to form new disulfide bonds. This method thus comprises a method for preventing, and/or reducing the recurrence of presbyopia by reducing the probability of forming new disulfide bonds. Particularly, this invention affects a change in the accommodative amplitude of the human lens by: (1) using various reducing agents that cause a change in the accommodative abilities of the human lens, and/or (2) the use of applied energy to affect a change in the accommodative abilities of the human lens. It is believed that by breaking bonds, such as disulfides, that crosslink lens fibers together and increase lens viscosity causing a hardening of the lens cortex and lens nucleus, the present invention increases the elasticity and the distensibility of the lens cortex, lens nucleus, and/or the lens capsule.

Presbyopia, or the loss of the accommodative amplitude of the lens, has often advanced in a typical person age 45 or older to the point where some type of corrective lens in the form of reading glasses or other treatment is required. It is to be understood that loss of accommodative amplitude can occur in persons much younger or older than the age of 45, thus the present invention is not to be construed as limited to the treatment of presbyopia in a person of any particular age. The present invention is most useful in a person whose accommodative amplitude has lessened to a point where restoration thereof to some degree is desirable. However the invention should not be limited to the correction of presbyopia, but may be used to prevent presbyopia from occurring.

In one embodiment of the present invention, the method of reversing or preventing presbyopia will result in an increase in the accommodative amplitude at least about by 0.5 diopters. In another embodiment of the present invention, the method of reversing or preventing presbyopia will result in an increase in the accommodative amplitude of at least about 2.0 diopters. In still another embodiment, the method of reversing or preventing presbyopia of the present invention will result in an increase in the accommodative amplitude by at least about 5 diopters. In another embodiment of the present invention, the method of reversing or preventing presbyopia of the present invention will result in an increase of the accommodative amplitude of the lens to restoration thereof to that of a lens with a normal accommodative amplitude of 2.5 diopters or greater. It is noted that while it is obviously most beneficial to restore the accommodative amplitude of the lens to a normal accommodative amplitude, lesser degrees of restoration are also beneficial. For example, in some cases advanced presbyopia can cause severe reduction in the accommodative amplitude, thus making a complete restoration of the amplitude improbable.

DETAILED DESCRIPTION

The accommodative amplitude of the lens is measured in diopters (D). The loss of accommodative ability begins at a very early age, such that by age 10 the average eye has 10 D, age 30, 5 D, and by age 40, only 2.5 D of accommodative power. The lens of a person who does not suffer from presbyopia (i.e. a person whose lens accommodates normally), will typically have an accommodative amplitude of about 2.5 diopters or greater. The terms "reversing presbyopia" or "treating presbyopia" as used herein mean increasing the accommodative amplitude of the lens.

As stated, inelasticity of the lens, or hardening thereof, is believed to be a contributing cause of presbyopia. The hardening of the lens can be due to an alteration of the structural proteins or an increased adhesion between the lens fibers. Additionally, it is believed that the lens viscosity also increases with age due to an increased concentration of certain chemical bond structures within the lens. In one embodiment, the present invention is directed to treating presbyopia by altering the molecular and/or cellular bonds between the cortical lens fibers so as to free their movement with respect to each other. The increased elasticity of the lens apparatus can restore lost amplitude of accommodation. Specifically, it is believed that disulfide bonds in the molecules comprising the structures of the eye responsible for proper accommodation are a substantial factor in the hardening of the lens and the concomitant loss of accommodative amplitude.

Thus, in one embodiment of the invention treatment process involves breaking the disulfide bond and then protonating the newly formed sulfur moiety with a reducing agent such as glutathione to impart a hydrogen atom thereto. The steps can be performed simultaneously or consecutively. In either case, the reducing agent can be present at the time the disulfide bond is broken in order to eliminate reformation of disulfide. That is, the reducing agent can introduce and bond a moiety onto the free sulfur after breaking the disulfide bond such that the likelihood of reformation of another disulfide bond is prevented or at least reduced. While the reducing agent may introduce a hydrogen atom onto the free sulfur, thus forming a sulfhydryl group (—SH), the resultant—SH groups can again be oxidized to form a new disulfide bond. Thus, it is advantageous to introduce a group into the free sulfur moiety, such as lower alkyls, methylating compounds, or other agents, which reduce the tendency of new disulfide bond formation. This method can result in a substantial prevention of the reoccurrence of presbyopia.

As stated, it is believed that the disulfide bonds form both between the lens fibers, between lens proteins, and between lens proteins and various thiols both within and on lens fibers. These bonds and substantially reduce the lens fibers' ability to easily move relative to each other and thus the ability of the lens to accommodate properly. While not wishing to be bound by any particular theory, the bonds may form by way of absorption of light energy, which causes the sulfhydryl bonds on the lens proteins to oxygenate removing a hydrogen atom from two adjacent—SH groups and creating water and a disulfide bond. Reducing the disulfide bonds requires hydrogen donors such as glutathione or other molecules. Other possible theories involve protein-thiol mixed disulfide bonds forming such as protein-S-S-glutathione or protein-S-S-cysteine. Glutathione therefore may be both part of the solution and part of the problem. The use of Glutathione in any treatment regimen therefore must be monitored carefully in light of the potential for an increase in undesirable bond formation.

The total refractive power of the lens is greater than what would be expected based on the curvature and the index of refraction. As stated, contraction of the ciliary muscle causes the ciliary body to move forward and towards the equator of the lens. This causes the zonules to relax their tension on the lens capsule, which allows the central lens to assume a more spherical shape. During accommodation, the main change is in the more central radius of curvature of the anterior lens surface, which is 12 mm in the unaccommodative state and can be 3 mm centrally during accommodation. Both the peripheral anterior and the posterior lens surfaces change very little in curvature during accommodation. The axial thickness increases while the diameter decreases. The central anterior lens capsule is thinner than the rest of the anterior capsule. This may explain why the lens bulges more centrally during accommodation. The thinnest portion of the capsule is the posterior capsule, which has a curvature greater than the anterior capsule in the unaccommodative state. The protein content of the lens, almost 33% by weight, is higher than any other organ in the body. There are many chemical compounds of special interest in the lens. For example, glutathione is found in high concentration in the lens cortex even though there is very little in the aqueous. Thus, the lens has a great affinity for glutathione and actively absorbs, transports and synthesizes glutathione. Approximately 93% of intralenticular glutathione is in the reduced form. Glutathione may be involved with maintaining the lens proteins, the sulfhydryl groups (—SH), in their reduced states. That is, after the disulfide bond is broken and the sulfur moieties are made available, glutathione can impart a hydrogen atom to form the sulfhydryl group thereby preventing or minimizing the reformation of a disulfide bond. In addition, ascorbic acid can also be found in very high concentrations in the lens. It is actively transported out of the aqueous and is at concentrations 15 times that found in the bloodstream. Both inositol and taurine are found at high concentrations in the lens for which the reason is not known.

According to one embodiment of the invention, the increase in the accommodative amplitude is accomplished by treatment of the outer lens region (the cortex) or the inner layer (the nucleus) with radiation, sonic or electromagnetic energy, heat, chemical, particle beam, plasma beam, enzyme, gene therapy, nutrients, other applied energy source, and/or any combination of any of the above sufficient to break the disulfide bonds believed responsible for the inelasticity of the lens. Chemicals are useful to reduce disulfide bonds that are believed to anchor lens fibers hence preventing their free movement and elasticity. By making the anterior cortex and/or the nucleus more elastic, viscosity is lowered and the lens is again able to assume its characteristic central bulge during accommodation.

Chemicals suitable for causing reduction include, by way of example only, glutathione, ascorbic acid, Vitamin E, tetraethylthiuram disulfyl, i.e., reducing agent, any biologically suitable easily oxidized compound, ophthalmic acid, inositol, beta-carbolines, any biologically suitable reducing compound, reducing thiol derivatives with the structure:

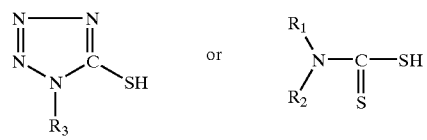

or sulfur derivatives with the structures:

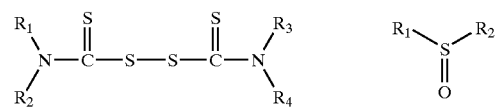

Wherein $R_1$, $R_2$, $R_3$ and $R_4$ are independently a straight or branched lower alkyl that may be substituted, e.g., by hydroxyl, lower alkoxy or lower alkyl carbonyloxy, their derivatives or a pharmaceutically acceptable salt thereof. Preferred exemplary reducing agents include diethyl dithiocarbamate, 1-methyl-1H-tetrazol-5-yl-thiol and 1-(2-hydroxyethyl)-1H-tetrazol-5-yl-thiol or and pharmaceutically acceptable salts thereof. Other useful compounds can be found in U.S. Pat. No. 5,874,455, which is hereby incorporated in its entirety by reference for background information. The above-mentioned chemicals are merely exemplary and other reducing agents that behave similarly by breaking the disulfide bond are included within the scope of this invention.

The chemical reducing agents can be used alone or in conjunction with a catalyst such as an enzyme. Enzymes and other nutrients suitable for causing or facilitating reduction include, for example, aldoreductase, glyoxylase, glutathione S-transferase, hexokinase, thiol reductase, thioltransferase, tyrosine reductase or any compatible reductase. The need for a source of applied energy for the reduction of the disulfide bonds may be met by the addition of glucose-6-phosphate, which is present within the lens but the enzyme, hexokinase that normally converts the glucose to the G6P energy state is rendered non-functional by the process of thiol oxidation. Again, it should be noted that the above-listed enzymes are exemplary and not an exhaustive list. The enzymes can be naturally present in the eye, or can be added to the eye together with or separate from the chemical reducing agent or energetic means disclosed herein. As such, other chemically and biologically comparable enzymes that help break disulfide bonds or behave similarly should be considered as within the scope of the present invention.

In one embodiment of the invention, the reduction of disulfide groups of the lens proteins to sulfhydryl groups is accomplished by delivering to the lens a compound such as glutathione, thiols, or others in sufficient quantities to reduce the disulfide bonds and other molecular and cellular adhesions. Other enzymes or chemicals that affect a methylation on the free sulfur atom include for example, methyl-methane thiosulfonate, methyl glutathione, S-methyl glutathione, S-transferase and other biologically compatible methylating agent. Use of emulsions such as nanocapsules, albumin microspheres, carrier molecules such as inositol, taurine or other biologically suitable means such as virus phages for delivering the reducing agent or enzymes to the lens is an integral part of this invention. The chemical reducing agent will typically be delivered in the form of a solution or suspension in an ophthalmically acceptable carrier. In some cases, the application of energy to affect or catalyze the reduction of the disulfide bonds as well as the disruption of other bonds and adhesions may be beneficial. The application of energy alone can be used to break the disulfide bonds. Applied energy can have any form, by way of example only, any of laser, ultrasound, particle beam, plasma beam, X-ray, ultraviolet, visible light, infrared, heat, ionizing, light, magnetic, microwave, sound, electrical, or other not specifically mentioned, can be used alone or in combination with the reducing agents to affect the treatment of presbyopia, or a combination of any of these types of energies.

In a similar manner, agents can be delivered to the lens capsule, which bind or interact with the capsule to affect greater elasticity or distensibility. Such agents either cause the capsule to shrink in surface area or increase the tension of the lens capsule on the peripheral anterior or posterior of the lens. Applied energy can have any form, by way of example only, any of laser, ultrasound, heat, particle beam, plasma beam, X-ray, ultraviolet, visible light, infrared, ionizing, light, magnetic, microwave, sound, electrical, or other not specifically mentioned can be used alone or in combination with the reducing agents to affect the treatment of presbyopia or a combination of any of these types of applied energy.

In another embodiment of the invention, applied energy can be used as a catalyst to induce or increase the rate of the reduction reaction. Thus, by applying energy, the peripheral portion of the capsule is preferentially affected, leaving the central 4 mm zone of accommodation unaffected. This allows the lens to assume a more accommodative state. The applied energy can also be applied alone to promote the reduction reaction and the cellular changes that ultimately affect the lens cortex. As examples, lasers useful in the present invention include: excimer, argon ion, krypton ion, carbon dioxide, helium-neon, helium-cadmium, xenon, nitrous oxide, iodine, holmium, yttrium lithium, dye, chemical, neodymium, erbium, ruby, titanium-sapphire, diode, femtosecond or attosecond laser, any harmonically oscillating laser, or any other electromagnetic radiation. Exemplary forms of heating radiation include: infrared, heating, infrared laser, radiotherapy, or any other methods of heating the lens. Finally, exemplary forms of sound energy that can be used in an embodiment of the invention include: ultrasound, any audible and non-audible sound treatment, and any other biologically compatible sound energy.

In still another embodiment of the present invention, radiation, such as ultraviolet light, visible light, infrared, microwave, or other electromagnetic energy may be placed in the eye to help break the disulfide bonds. This would then make it possible for the reduction of the disulfide bonds to occur.

The applied energy used with various embodiments and methods of the present invention could be applied through either contact with the sclera or cornea, non-contact techniques, or through intraocular methods of delivery. More than one treatment may be needed to affect a suitable increase in the accommodative amplitude. When more than one modality of treatment is desirable, chemical treatment can be administered prior to, after, or simultaneously with the application of energy.

What is claimed is:

1. A method for increasing an accommodative amplitude of a lens comprising applying localized energy to an area to be treated and administering a pharmaceutically sufficient quantity of a biologically acceptable chemical substance to break chemical bonds between and/or within lens fibers.

2. The method of claim 1, wherein said biologically acceptable chemical substance comprises glutathione, thiols and derivatives thereof.

3. A method for increasing an amplitude of accommodation of a human eye having a lens and a ciliary muscle comprising administering a pharmaceutically sufficient quantity of a biologically acceptable reducing agent to affect a change in an elasticity of the lens; and treating the human eye with applied energy.

4. The method of claim 3, wherein the biologically acceptable reducing agent is selected from the group consisting of glutathione, thiols and derivatives thereof.

5. A method for increasing an accommodative amplitude of a lens comprising:
   breaking interlenticular and/or intralenticular fiber adhesions to free the fibers to move relative to each other;
   reducing a likelihood of formation of further interlenticular and/or intralenticular fiber adhesions; and
   applying energy to the lens.

6. The method of claim 5, wherein breaking and/or reducing a likelihood of formation of interlenticular and/or intralenticular fiber adhesions further comprises applying an enzyme capable of breaking and/or reducing a likelihood of formation of said interlenticular and/or intralenticular fiber adhesions.

7. The method of claim 5, wherein breaking and/or reducing a likelihood of formation of interlenticular and/or intralenticular fiber adhesions further comprises applying a chemical catalyst capable of promoting a catalytic reaction.

8. A method for increasing an accommodative amplitude of a lens comprising applying localized energy to area to be treated and administering a pharmaceutically sufficient quantity of a biologically acceptable chemical substance to break and/or reduce a likelihood of formation of the chemical bonds between two sulfur groups lens fibers.

9. A pharmaceutical composition for increasing an accommodative amplitude of a lens comprising thiol transferase, glutathione, nicotine adenine dinucleotide phosphates wherein the composition's accommodative improvement effect is further adapted to be induced or increased by applying energy to the composition.

10. The pharmaceutical composition of claim 9, further comprising a biocompatible carrier.

11. The pharmaceutical composition of claim 9, further comprising a viral phage.

12. The pharmaceutical composition of claim 10, wherein the composition is adapted to be administered topically.

13. The pharmaceutical composition of claim 9, wherein the composition is adapted to be administered systematically.

14. The pharmaceutical composition of claim 9, further comprising a photo reactive compound.

15. The pharmaceutical composition of claim 14, wherein the composition is adapted to be activated by introduction of applied energy.

16. The pharmaceutical composition of claim 9, wherein the thiol transferase is present in an amount of 0–20 wt%.

17. The pharmaceutical composition of claim 9, wherein the glutathione is present in an amount of 0–20%.

18. The pharmaceutical composition of claim 9, wherein nicotine adenine dinucleotide phosphate is present in an amount of 0–20%.

19. The pharmaceutical composition of claim 9, wherein the glutathione is S-glutathione.

20. The method of claim 1, wherein the chemical bonds are disulfide bonds.

21. The method of claim 1, wherein applying comprises applying localized energy including at least one of radiation, sonic energy, electromagnetic energy, heat, chemical energy, particle beam energy, plasma beam energy, an enzyme, gene therapy, and nutrients.

22. The method of claim 3, further comprising reducing a likelihood of formation of disulfide bonds in the human eye.

* * * * *

UNITED STATES PATENT AND TRADEMARK OFFICE
CERTIFICATE OF CORRECTION

| | | |
|---|---|---|
| PATENT NO. | : 6,923,955 B2 | Page 1 of 1 |
| APPLICATION NO. | : 10/050879 | |
| DATED | : August 2, 2005 | |
| INVENTOR(S) | : Till et al. | |

It is certified that error appears in the above-identified patent and that said Letters Patent is hereby corrected as shown below:

In the cover page, under "(56)  References Cited, change the first cited U.S. Patent Document from "817,630 A  *  4/1906 Delaunay-Belleville ... 514/18" to --5,817,630 A  *  10/1998 Hofmann et al. ... 514/18--.

| Column | Line | |
|---|---|---|
| 4 | 16 | Change "eve" to --eye--. |
| 8 | 23 | Before "area" insert --an--. |

Signed and Sealed this

Sixth Day of February, 2007

JON W. DUDAS
*Director of the United States Patent and Trademark Office*